United States Patent [19]
Shalon et al.

[11] Patent Number: 6,036,855
[45] Date of Patent: Mar. 14, 2000

[54] METHOD AND APPARATUS FOR PACKING AND SEALING CHROMATOGRAPHIC COLUMNS

[75] Inventors: Yehuda Shalon; Ilya B. Nykin; Tadmor Shalon, all of St. Louis, Mo.

[73] Assignee: MODcol Corporation, St. Louis, Mo.

[21] Appl. No.: 08/937,301

[22] Filed: Sep. 15, 1997

Related U.S. Application Data

[62] Division of application No. 08/798,610, Feb. 11, 1997, abandoned.

[51] Int. Cl.[7] .................................................. B01D 15/08
[52] U.S. Cl. ...................... 210/198.2; 210/656; 210/657
[58] Field of Search ........................ 210/635, 656, 210/657, 659, 198.2, 232, 238; 141/12, 73, 80; 95/82

[56] References Cited

U.S. PATENT DOCUMENTS

| D. 285,290 | 8/1986 | Shalon et al. | 210/656 |
|---|---|---|---|
| 4,350,595 | 9/1982 | Gunkel | 210/656 |
| 4,361,482 | 11/1982 | Teetz et al. | 210/198.2 |
| 4,451,365 | 5/1984 | Sättler et al. | 210/198.2 |
| 4,597,866 | 7/1986 | Couillard | 210/198.2 |
| 4,675,105 | 6/1987 | Martin et al. | 210/198.2 |
| 4,710,289 | 12/1987 | Wermuth et al. | 210/198.2 |
| 4,719,011 | 1/1988 | Shalon et al. | 210/198.2 |
| 4,737,292 | 4/1988 | Ritacco et al. | 210/198.2 |
| 4,769,141 | 9/1988 | Couillard | 210/198.2 |
| 4,882,047 | 11/1989 | Shalon | 210/198.2 |
| 4,891,133 | 1/1990 | Colvin, Jr. | 210/198.2 |
| 5,137,628 | 8/1992 | Hart et al. | 210/198.2 |
| 5,169,522 | 12/1992 | Shalon et al. | 210/198.2 |
| 5,192,433 | 3/1993 | Shalon | 210/198.2 |
| 5,213,683 | 5/1993 | Mann | 210/198.2 |
| 5,423,982 | 6/1995 | Jungbauer et al. | 210/198.2 |
| 5,462,659 | 10/1995 | Saxema et al. | 210/656 |
| 5,531,810 | 7/1996 | Fullemann | 210/198.2 |

*Primary Examiner*—Ernest G. Therkorn
*Attorney, Agent, or Firm*—Howell & Haferkamp, L.C.

[57] ABSTRACT

A chromatographic device in which a chromatographic column pivots on a compression cylinder. Prior to pivoting, one end of the column is sealed with an end cap, the column is at least partially filled with a chromatographic medium and a piston is frictionally engaged within the column. The chromatographic column is then pivoted onto the compression cylinder, and the compression device is operated to push the piston into the column with a telescoping rod. The telescoping rod is then retracted, leaving the piston in place. The chromatographic column is then removed from the compression cylinder. A spring assembly is then inserted into column above the piston, and held in place with a torque mechanism mounted on the chromatographic column. The torque mechanism includes a bolt that can be tightened to provide a variable spring pressure against the piston. A rotating coupling is provided so that the chromatographic column and compression column can be operated in at least two different directions to facilitate the removal of the medium from the chromatographic column after use.

23 Claims, 7 Drawing Sheets

METHOD AND APPARATUS FOR PACKING AND SEALING CHROMATOGRAPHIC COLUMNS

This is a divisional of application Ser. No. 08/798,610 filed on Feb. 11, 1997, now abandoned.

BACKGROUND OF THE INVENTION

1. Field of the Invention

The present invention relates to the field of liquid chromatography. More particularly, the present invention is directed to an improved method for sealing liquid chromatographic columns and improved closure members for use therewith.

2. Description of the Prior Art

Chromatography is a method for separating individual compounds in a mixture by distributing the compounds between heterogenous phases. A column packing material (or media), forming a stationary phase, generally has a large surface area through which a liquid mobile phase is allowed to flow. Chemical compounds in the mobile phase are maintained in the system for a time that is dependent upon the affinity of the particular compounds for the stationary phase. Multiple component mixtures can, with chromatography, be separated into single components in a single step procedure.

Chromatographic separations can be carried out efficiently in columns slurry packed with microparticulate media. The slurry is uniformly and rapidly compacted into a column under pressure. The slurry is maintained at very high pressure and density to achieve the most efficient end results.

Figure 1:
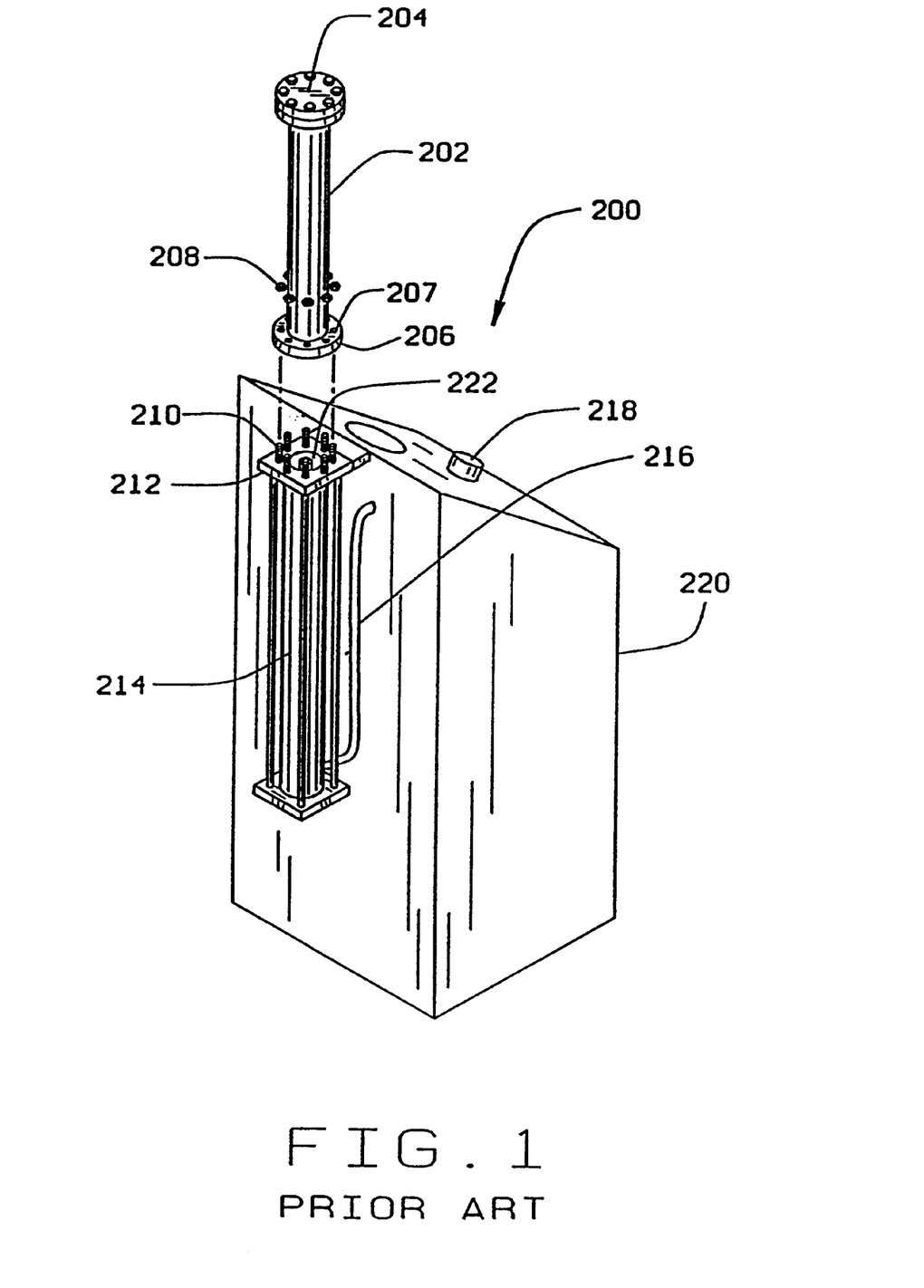
FIG. 1 is a perspective view of a prior art chromatographic column and pressing apparatus.

A chromatographic column includes a cylindric column body, a fixed end plate covering one end of the column body, a piston slidable within the column body, an intake opening through the piston, a discharge opening through the end plate, a first porous frit secured to the piston and covering the intake opening, and a second porous frit secured to the end plate and covering the discharge opening. A slurry containing the packing material, such as a granular silica or polymeric media, is placed within the column body and the piston is moved toward the fixed end plate to compress the slurry. The pores of the frits are sized to permit the liquid of the slurry to flow out the discharge opening while preventing discharge of the packing material. An example of a prior art chromatographic column 202 and a compression device 220 which together comprise a chromatographic apparatus 200 is shown in FIG. 1. Column 200 is placed on the compression device 220 on a plate 212 at the end of a hydraulic compression cylinder 214. Column 200 has a flange 206 with a number of mounting holes 207 that fit over a group of threaded rods or bolts 210 extending upward from plate 212. Once mounted, nuts 208 secure the flange onto plate 212. A piston 222 is secured to the end of a telescoping rod (not shown) that can be controlled by one or more controls 218 on pressing apparatus 220. The piston 222 and telescoping rod are typically powered by a pneumatic pump though line 216, which moves the telescopic rod. The piston 222 includes an intake opening and a feeding tube (neither of which are visible in FIG. 1), the latter of which can be mounted in a recess on either plate 212 or flange 206 or both to prevent the tube from being crushed when the column 202 is secured to plate 212. A chromatographic slurry is then loaded into the upper end of column 202, and end plate 204 is secured in place. End plate 204 includes a discharge opening for attaching an outlet tube. (of course, the terminology "intake" and "outlet" are arbitrary, because the direction of flow may be reversed, i.e., changed from the piston to the end cap or from the end cap towards the piston.)

Conventionally, when the chromatographic media within chromatographic column 202 is packed, a telescoping rod pushes piston 222 into the column. This compression packs the packing material to a predetermined pressure (which may typically be around 1,000 to 5,000 p.s.i., but these value are merely exemplary rather than limiting). It would be advantageous if the column were constructed so that the rod were not connected to the piston or the column (other than by pressing against the piston) so that the piston could remain in a compressed position within the column body, at least for a period of time, after the rod is retracted. Previous chromatographic columns have not been designed to allow a packed column to be removed from the pressing apparatus and set aside for future use in this manner, but it would be advantageous if it were possible to do so in this manner. In addition, pressing apparatuses have, until now, been constructed so that the apparatus can only be operated with the telescoping rod extending from its cylinder in only one orientation. It would be advantageous if, instead, the apparatus could be operated to extend the rod in either an upward or a downward orientation. Moreover, it would be advantageous if the column could be pivoted on the pressing apparatus to facilitate mixing of the chromatographic medium inside the column.

SUMMARY OF THE INVENTION

One aspect of the invention therefore is a chromatographic device comprising a chromatographic column having a hollow tube with first and second opposite open ends, a mounting member secured to the column generally adjacent the first end, and an end cap covering the second end; a piston slidable within the tube; and a pressing apparatus having a column receiving portion engageable with the mounting member of the chromatographic column, and a pressing mechanism adjacent the column receiving portion; the column receiving portion of the pressing apparatus and the mounting member of the chromatographic column being shaped and configured for pivotal movement of the chromatographic column relative to the pressing apparatus between an open position in which the first end of the tube is spaced from the pressing apparatus and a closed position in which the first end of the tube is adjacent the pressing apparatus, the column being moveable relative to the pressing apparatus to an aligned position in which the first end of the tube is aligned with the pressing mechanism, the pressing mechanism being configured for pressing the piston into the tube and toward the second end of the tube.

According to another aspect of the invention, there is provided a chromatographic device comprising a piston a chromatographic column comprising a hollow tube with first and second opposite open ends, a mounting member secured to the column generally adjacent the first end, and an end cap covering the second end; and a pressing apparatus having a column receiving portion engageable with the mounting member of the chromatographic column, and a telescoping rod moveable between a retracted position and an extended position; wherein the piston is pressed towards the second end of the tube when the column is in the closed position and the telescoping rod is extended and the piston is separate from the telescoping rod and insertable into the chromatographic column and into sliding, sealing engagement therewith, so that the telescoping rod engages the piston within the chromatographic column when the pressing apparatus is operated to extend the telescoping rod, and is disengaged when the pressing apparatus is operated to retract the telescoping rod.

According to yet another aspect of the invention, there is provided a chromatographic device comprising a hollow tube having a first end and a second end, the second end being closed; a piston inside the hollow tube; a chromatographic medium between the piston and the second end; and a compression spring inside the tube and configured for exerting a force on the piston to press the piston against the chromatographic medium.

According to still another aspect of the invention, there is provided a chromatographic device comprising a chromatographic column having a hollow tube with first and second opposite open ends, a mounting member secured to the column generally adjacent the first end, and an end cap covering the second end; a piston slidable within the tube; and a pressing apparatus having a stationary portion, a column receiving portion engageable with the mounting member of the column to securely hold the column, and a pressing mechanism adjacent the column receiving portion and configured for moving the piston inside the column when the column is securely held by the column receiving portion, the column receiving portion and pressing mechanism being operatively connected to the stationary portion for pivotable movement of the column receiving portion between different first and second positions, the pressing apparatus being configured to push the piston within the tube towards the second end of the hollow tube when the column receiving portion and pressing mechanism are in the first position and in the second position.

According to another aspect of the invention, there is provided a method of operating a chromatographic device comprising a chromatographic column, the method comprising the steps of filling a portion of the chromatographic column with a chromatographic medium; fitting a sealingly engageable piston into the chromatographic column; exerting a force on the piston to move the piston into the column thereby to compress the chromatographic medium; relieving the force on the piston; and inserting a compression spring inside the chromatographic column after said force on the piston has been relieved wherein the spring presses the piston against the chromatographic medium.

It is thus an object of the invention to provide a chromatographic column and pressing apparatus that can suitably compress media in the chromatographic column without permanent engagement of a rod and a piston within the column.

It is a further object of the invention to provide a chromatographic column that can be compressed, removed from the pressing apparatus, and compressibly sealed so that a chromatographic medium disposed within the column remains in a state ready for use.

It is an additional object of the invention to provide a chromatographic column that, once compressibly sealed as above, is resistant to void formation.

It is yet an further object of the invention to provide a pivoting attachment for attaching a chromatographic column to a pressing apparatus whereby the chromatographic column can be pivoted to thereby agitate a chromatographic medium within the column.

These and additional objects of the present invention will become clear to one skilled in the art upon reference to the figures and to the detailed description below.

DETAILED DESCRIPTION OF THE INVENTION

Figures 2, 3:
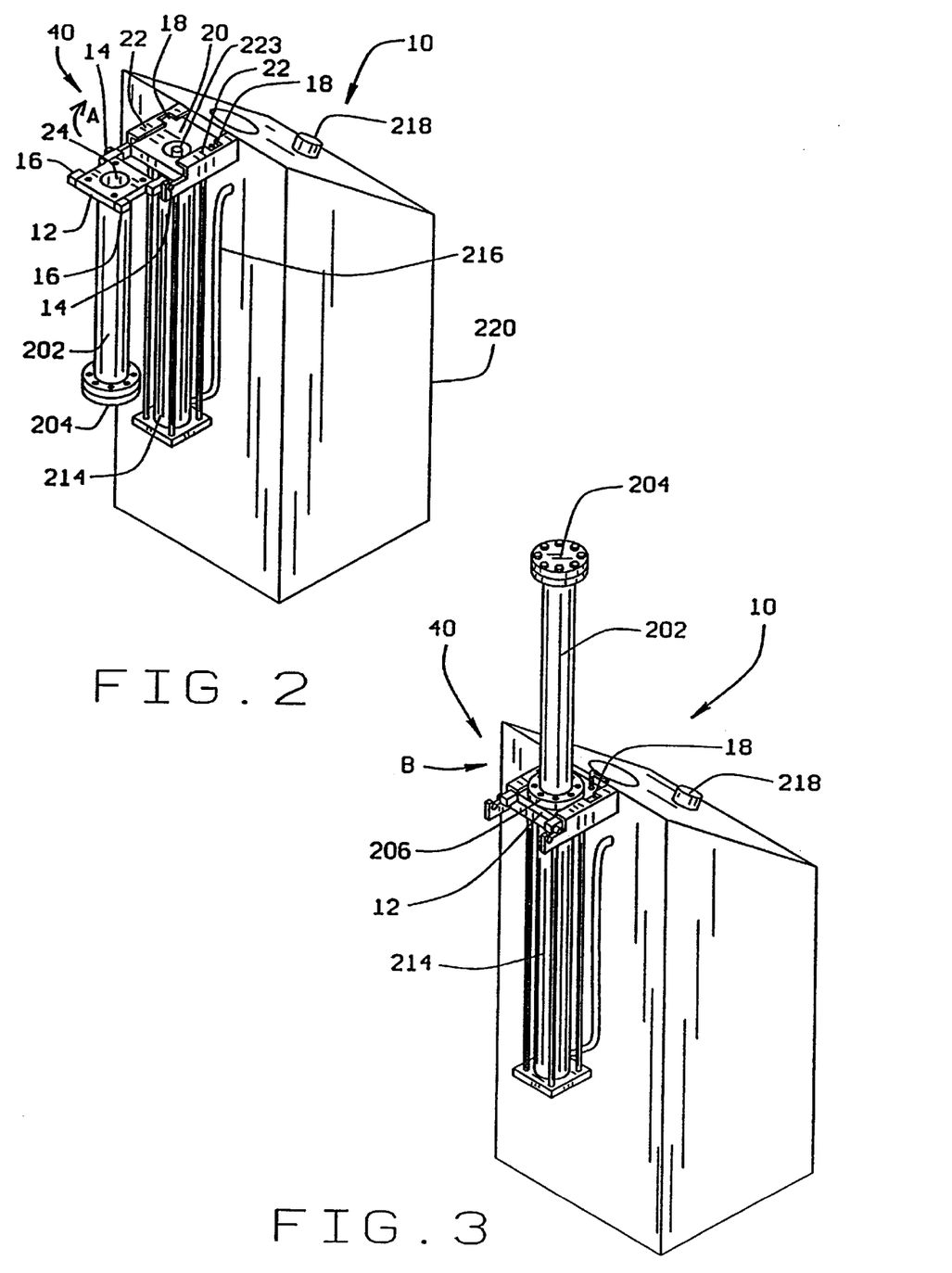
FIG. 2 is a perspective view of an embodiment of a chromatographic column and pressing apparatus in accordance with the invention showing the chromatographic column operably disengaged from the pressing apparatus.
FIG. 3 is a perspective view of the embodiment of FIG. 2 in which the chromatographic column is operably engaged with the pressing apparatus.

FIG. 2 shows an embodiment of the inventive chromatographic assembly 10 in accordance with one aspect of the invention. The inventive assembly comprises a pressing apparatus 220 and a chromatographic column 202 comprising a hollow tube. Chromatographic column 202 may be used for chromatography either mounted on pressing apparatus 220 or removed therefrom, in a manner to be explained below. Pressing apparatus 220 comprises a cylinder 214 housing a telescoping rod or pressing mechanism 223, preferably powered by hydraulic pressure, which is supplied by pressure line 216 in the illustrated embodiment. One end of chromatographic column 202 is covered by an end plate 204 prior to loading with a suitable chromatographic medium (not shown). The other end of chromatographic column 202 has a plate or mounting member 12 proximate thereto. Plate 12 may either be integral to column 202, secured to column 202 by bolts or screws, or secured in any other fashion that does not interfere with the pivoting action described in more detail in conjunction with FIG. 4. (If it is desired to omit the pivoting feature, this limitation need not apply.) Prior to pivoting, a piston (not shown in FIG. 2) is placed into opening 24 of column 202 in a manner described in detail below so that the chromatographic medium does not spill out of column 202 when it is pivoted. FIG. 3 shows apparatus 10 when the chromatographic column 202 has been pivoted in the direction of arrow A (in FIG. 2) and slid in the direction of arrow B so that the piston is positioned to receive compressional forces from rod 223.

Figure 4:
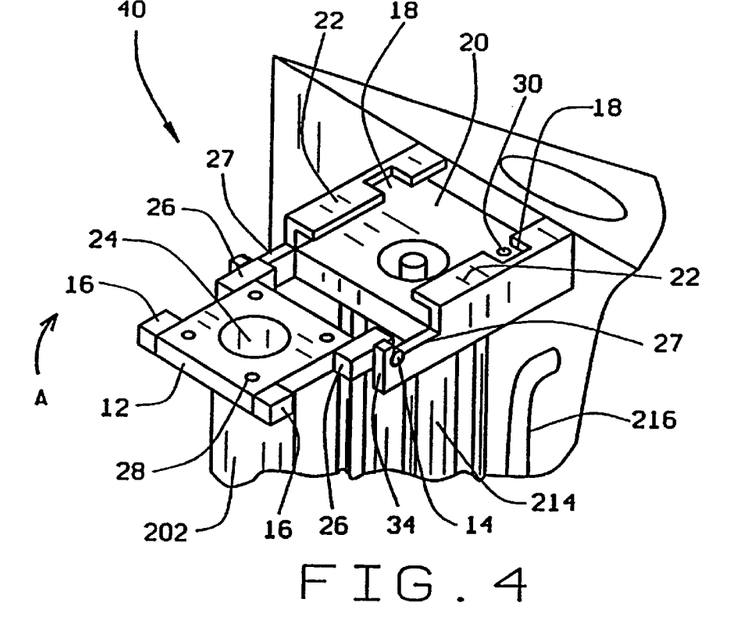
FIG. 4 is an enlarged, fragmented, perspective view of a portion of FIG. 2 showing one position of the pivoting arrangement of the chromatographic and compression cylinder.
Figure 5:
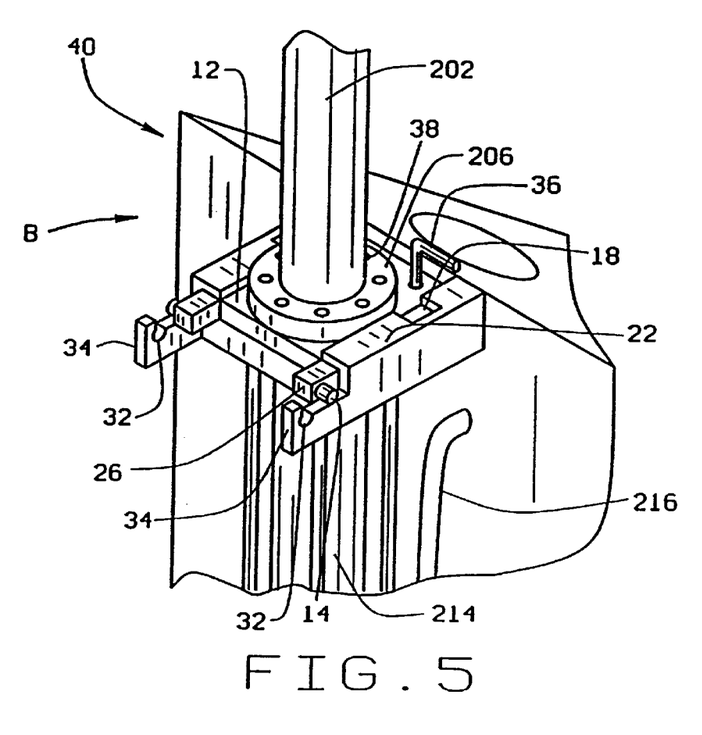
FIG. 5 is an enlarged, fragmented, perspective view of a portion of FIG. 3 showing another position of the pivoting arrangement of the chromatographic and compression cylinder.

FIGS. 4 and 5 show in more detail how the column 202 is received by and pivoted on the receiving portion 20 of cylinder 214 in accordance with one aspect of the invention. Referring to FIG. 4, plate 12 on chromatographic column 202 includes flanges 16 and 26. Each of the pair of flanges 26 is provided with a pivoting member 14 that can be inserted into a pivoting member receptacle 32, the latter being best seen in FIG. 5 near the end of cantilevered arms 27 extending from the sides of receiving portion 20 of cylinder 214. Retaining arms 34 may be provided to prevent the column 202 from accidently becoming unseated and falling off. Returning to FIG. 4, pivoting members 14, in conjunction with the pivoting member receptacles, allow column 202 to be pivoted in the direction of arrow A from the open position shown in FIG. 4 in which a chromatographic medium may be loaded into column 202 prior to the insertion of a piston. When column 202 is pivoted in the direction of arrow A, flanges 16 enter slots 18 of engageable holding members 22 included on receiving portion 20 so that the flanges rest directly on receiving portion 20 in an aligned position.

Referring to both FIGS. 4 and 5, after column 202 is pivoted in the direction of arrow A, it may be slid in the direction of arrow B into a closed position, so that flanges 16 no longer align with slots 18 and column 202 is held in place against further pivoting by the engagement of flanges 26 and 16 in engageable holding member 22. In this position, an end of column 202 is aligned with the telescoping rod 223 in a position in which telescoping rod 223 can extend to press the piston into column 202 towards the opposite end of column 202. Moreover, after sliding, at least one hole 28 provided in plate 12 aligns with at least one hole 30 that extends at least partially through receiving portion 20, so that a locking pin or screw 36 can be placed through both holes 28 and 30 to prevent sliding disengagement of column 202 from cylinder 214 until locking pin or screw 36 is removed. In the position shown in FIG. 5, the piston (not shown) that was placed in opening 24 of column 202 is aligned over opening 32 of cylinder 214 so that rod 223 may be pushed against the piston to compress the chromatographic media in column 202. According to another aspect of the invention, the piston need not be fixedly attached to rod 223 during compression, so that rod 223 may be withdrawn from chromatographic column 202 without withdrawing the piston.

Figures 6, 7:
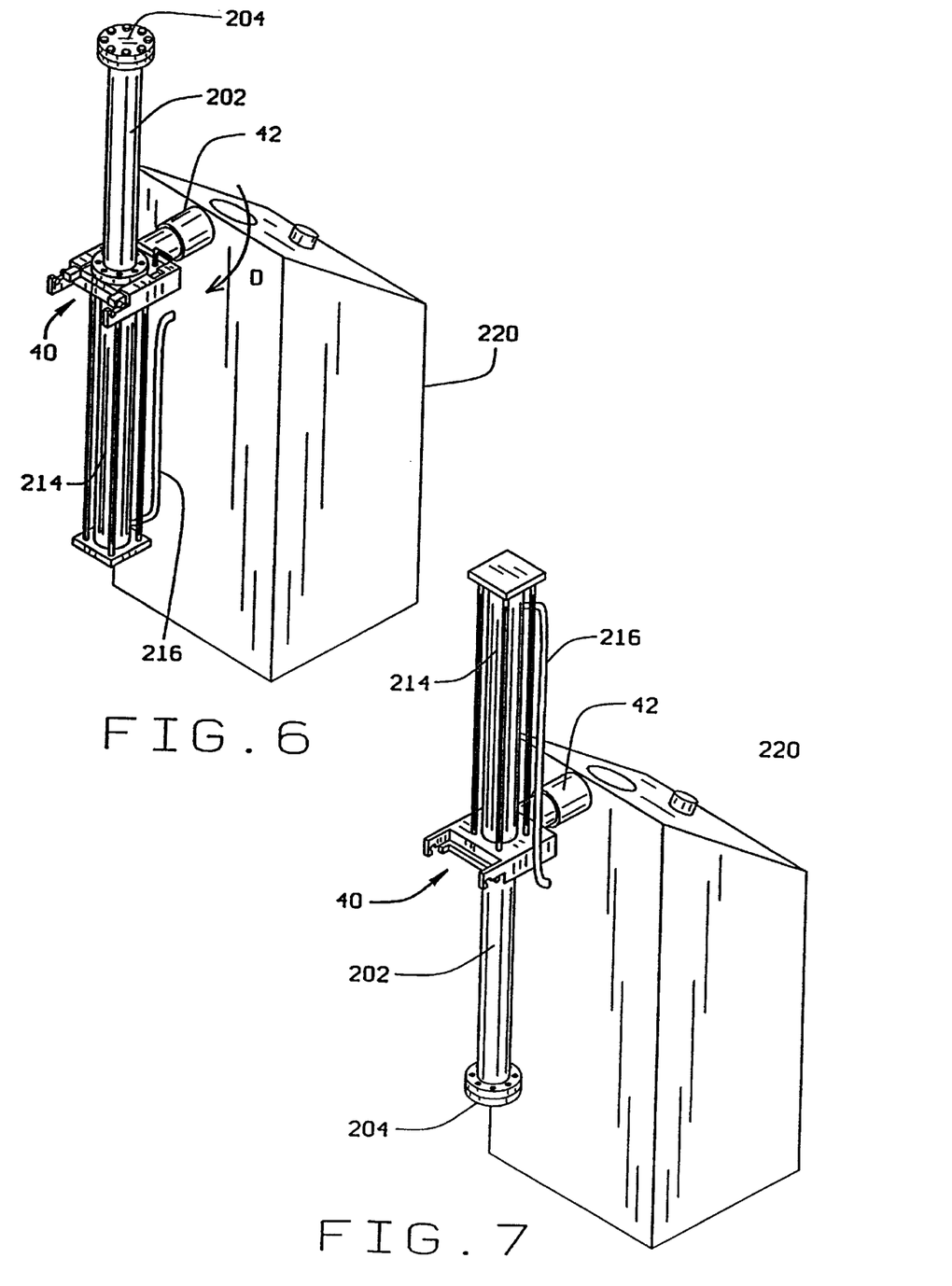
FIG. 6 is a perspective view of an alternate embodiment of the invention showing a pivoting arrangement in which the compression cylinder can also be pivoted.
FIG. 7 is a perspective view of the embodiment of the invention shown in FIG. 6 with the compression cylinder in a position to provide compression in an opposite direction.

Referring to FIGS. 6 and 7, the pivoting and sliding assembly 40 according to another aspect of the invention may be mounted on pressing apparatus 220 with a rotating joint 42 that rotates in a direction illustrated by arrow D (or in the opposite direction, or in both directions). Rotating joint 42 may be either manually operated or powered, e.g., by electrical or hydraulic power. Because cylinder 214 in the illustrated embodiment is powered by a flexible (or at least repositionable) hydraulic line 216, rotating joint 42 allows compression to be applied with chromatographic column 202 in either the position shown in FIG. 6 or the position shown in FIG. 7 (or, if additional supporting hardware or at least sufficient friction is provided, at any position between). Rotating joint 42 thus provides an additional advantage of allowing chromatographic medium in column 202 to be compressed by a piston (not shown in FIGS. 6 and 7) moving either upward or downward, or in some other orientation. It will be recognized that the additional pivoting motion provided by rotating joint 42 can also be used advantageously in an apparatus not provided with a pivoting and sliding assembly 40.

After use, chromatographic column 214 may need to be emptied and the contents discarded, recycled, or detoxified. Preferably, this is done by removing end cap 204 from column 214 and rotating the column into the position shown in FIG. 7. In this position, pressing apparatus 220 may be operated to push a piston (not shown in FIG. 7) in column 202 in a downward direction, so that the contents of column 202 are emptied downward into a collection bucket (also not shown in FIG. 7) directly beneath the end of the column. This provides an improvement over prior art pressing apparatuses that pack and compress columns in only one direction as shown in FIG. 6. Emptying columns in the position shown in FIG. 6 results in the chromatographic medium being pushed out the top of column 202, which may be messy and even hazardous, depending upon the chemicals in the medium. Providing a rotating joint 42 makes it possible to pack the chromatographic column 202 by applying pressure in an upward direction, and to empty the column by applying pressure in a downward direction, the latter operation neatly emptying the column into the collection bucket. Referring to FIG. 6, the pressing apparatus 220 includes a portion that remains stationary while the pivoting and sliding assembly 40 rotates between at least two positions. In either of the two positions, a piston (not shown) inside of column 202 is pushed towards the end of column 202 opposite the pivoting and sliding assembly 40.

Figure 8:
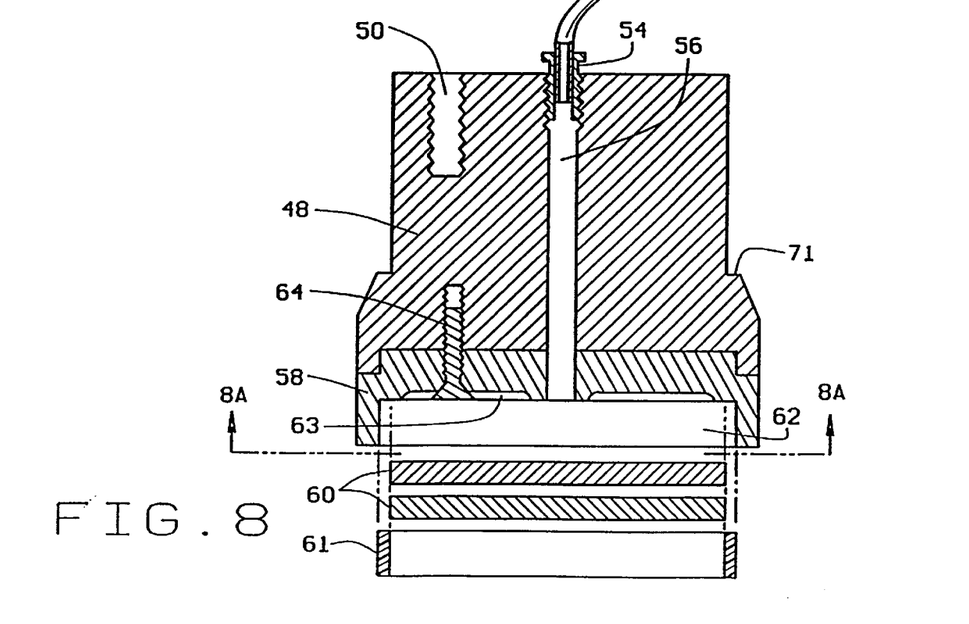
FIG. 8 is a longitudinal section exploded view of a main portion of a piston body in accordance with the invention.
Figure 9:
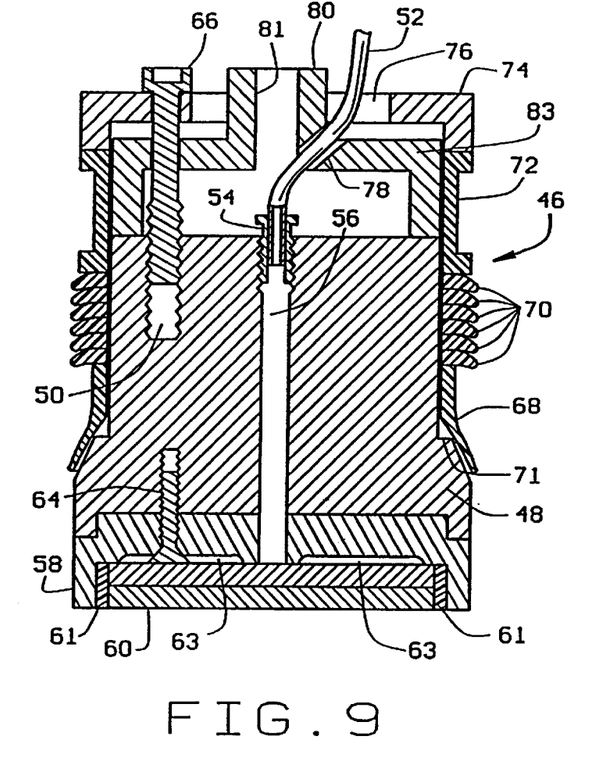
FIG. 9 is a longitudinal section view of an assembled piston in accordance with the invention.

FIGS. 8 and 9 show a piston 46 in accordance with another aspect of the invention that may be used to pack column 202 without the piston being fixedly attached to a rod. Referring first to FIG. 8, a piston body 48 is provided, having one or more threaded holes 50 (only one of which is shown) for attachment of a piston cap 83 with a bolt 66, as shown in FIG. 9. Preferably a plurality of threaded holes 50 are provided for reasons that will become apparent below.

Returning to FIG. 8, a frit holder or seat 58 is provided at an end of piston head 48 that is intended to face the chromatographic media. Frit holder 58 may either be integral to piston head 48 or it may be removably attached to piston head 48, such as by one or preferably a plurality of screws 64, as shown in FIG. 8. One or more porous frits 60 are inserted within frit holder 58, and are held in place with a circumferential O-ring 61 that is machined to fit tightly around the frits 60 when the ring 61 and frits 60 are inserted into frit holder 58. Ring 61 is preferably made of polytetrafluoroethylene (PTFE), but could be made of other materials, perhaps depending upon the chemistry of the chromatographic separation.

Figure 8A:
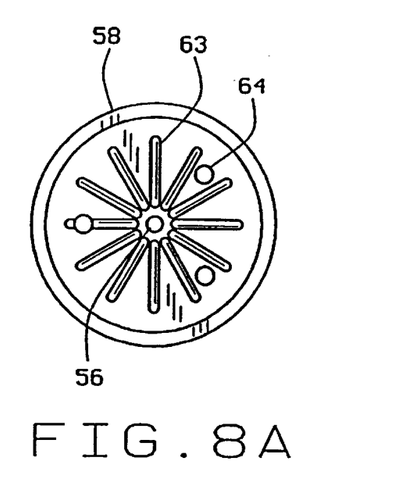
FIG. 8A is a cross-sectional view taken along the plane 8A—8A of FIG. 8 to illustrate radial grooves that facilitate passage of liquid through frits in the piston.

Frits 60 allow passage of a fluid containing substances in solution to be separated while not allowing solid particles in the chromatographic medium (usually, but not necessarily, fine silica particles) to escape from the chromatographic column. The solution is supplied through a feeding tube 52 which communicates with passageway 56 through piston body 48 through a sealing connection at 54. Radial grooves 63 (shown in another view facing the reader in FIG. 8A) on a surface of frit seat 58 at a continuation of passageway 56 allow the solution to be spread more evenly across the surface of frits 60 to facilitate entry of the solution into the chromatographic column when the piston is inserted therein.

An assembled view of the piston is shown in FIG. 9. A pusher head 83 is placed on an end of piston body 48 opposite frits 60. This pusher head has a channel 78 through which feeding tube 52 is inserted and a central portion 80 that is dimensioned to contact rod 223 (not shown in FIG. 9) so that pressure provided by rod 223 pushes piston 46 into the chromatographic column in a manner to be described below. The central portion 80 may optionally include a internal cylindrical portion that is tapped, so that it can be attached to a pushing rod similar to rod 223, but having a threaded end. It is, however, a feature of the invention that the pushing rod need not be so attached, thereby allowing the rod to be withdrawn from the chromatographic column without also withdrawing the piston, as otherwise would be required, and thus allowing the chromatographic column 202 containing a packed medium to be removed from the pressing apparatus. To hold pusher head 83 in place, and to provide a sealing engagement with the chromatographic column, a series of rings (preferably PTFE, but, depending upon the chemistry of the chromatographic separation, other flexible materials may be used) are placed around the assembled piston head 48 and pusher head 83. These rings include a ring 68 that rests on or about shoulder 71 of piston head 48, several compressible V-rings 70 (so called because the circumference of each ring has a nesting, V-shaped cross section), and a relatively stiff outer ring 72. Finally, an outer cap 74 is provided to hold the assembly together with a bolt 66 that engages a tapped hole 50 in piston body 48. Preferably a plurality of bolts 66 and holes 50 are provided. Feeding tube 52 is passed through a hole 76 in outer cap 74.

Figures 10, 11:
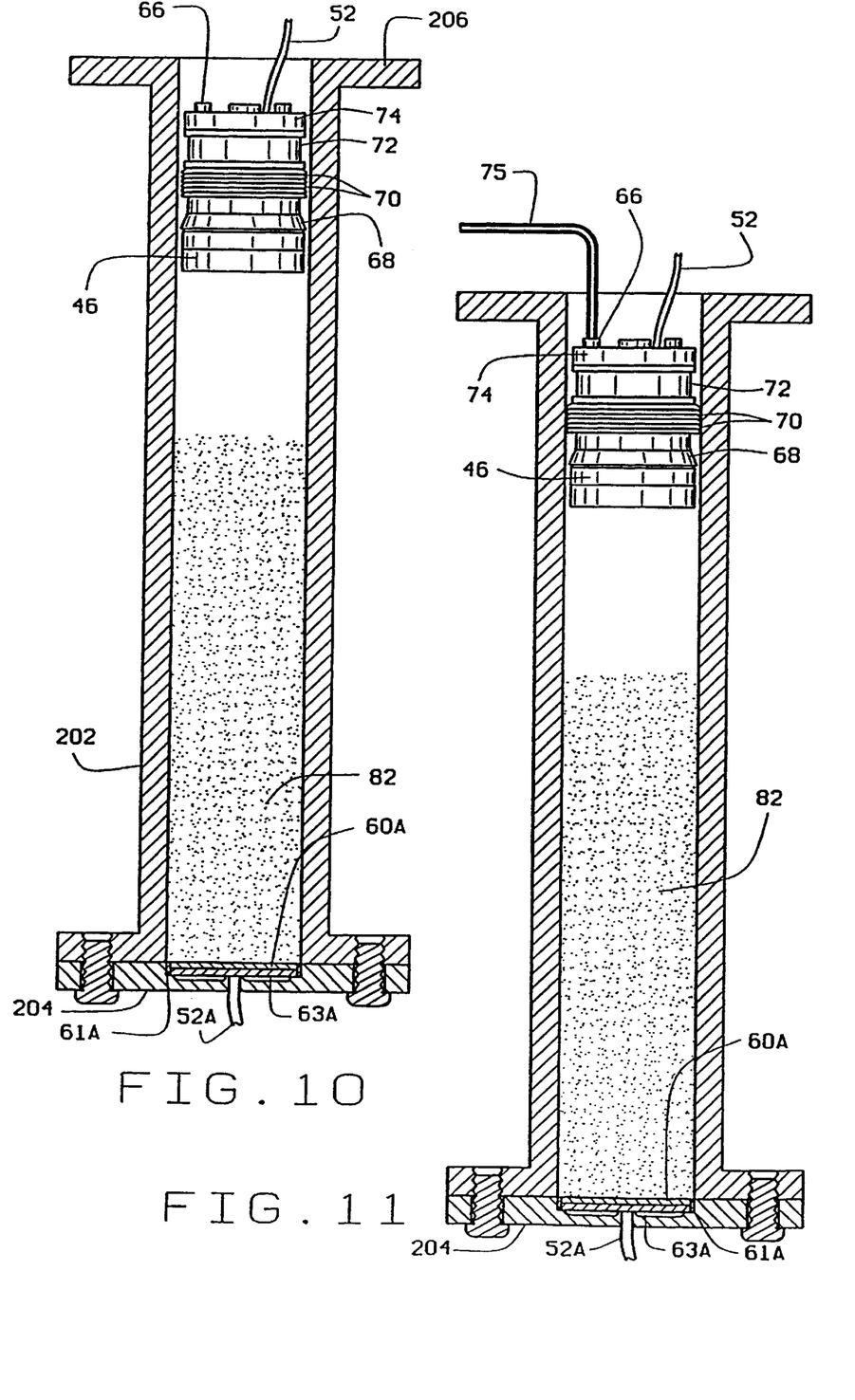
FIG. 10 is a longitudinal section view of a chromatographic column with the piston of FIG. 9 inserted.
FIG. 11 is a longitudinal section view of the assembly of FIG. 10 showing the expansion of the piston in the chromatographic column to provide a tight fit.

Outer cap 74 provides a variable amount of pressure on V-rings 70, so that when bolts 66 are torqued, pressure from the outer cap 74 compresses the set of rings 68, 70, and 72, forcing V-rings 70 to expand slightly so that they exert pressure on the inside wall of chromatographic column 202 and form a tightly sealing engagement therewith as best seen in FIGS. 10 and 11, which show the column 202 and attachments (except for piston 46) in a side sectional view. The tightness of the seal is adjusted so that the piston is pushed into column 202 by the pressing apparatus and remains in place when column 202 is removed from the pressing apparatus. FIG. 10 shows the piston 46 inserted in chromatographic column 202, which is partially filled with a chromatographic medium slurry 82 to be compressed. (The looseness of the fit of piston 46 inside column 202 is considerably exaggerated in the figures to show that the tightness of V-rings 70 increases when bolts 66 are torqued. In reality, the entire piston is in sliding, sealing engagement inside column 202.) Cap 204 is also shown on chromatographic column 202 in FIG. 10, showing a frit arrangement 60A with compressible ring 61A, radial grooves 63A and outlet tube 52A analogous to the arrangement of the frits, ring, grooves and tube of piston 46. (It will be understood by those skilled in the art that the designation of one of the tubes as a "feeding" tube and the other as an "outlet" tube is arbitrary, inasmuch as column 202 can be operated with fluid flowing through it in either direction.) By applying torque to the bolts 66, outer cap 74 compresses rings 72, 70, and 68, causing V-rings 70 to increase their compressive force against the inner surface of column 202.

It should be apparent from the description that various types of pistons and piston assemblies other than that illustrated in the Figures can be used in conjunction with the invention, preferably pistons that can be pushed by a rod that is not fixedly attached to the piston, and from which the rod can later be withdrawn with the piston remaining in place due to friction or sideways compression, in accordance with one of the aspects of the invention.

Figures 12, 13:
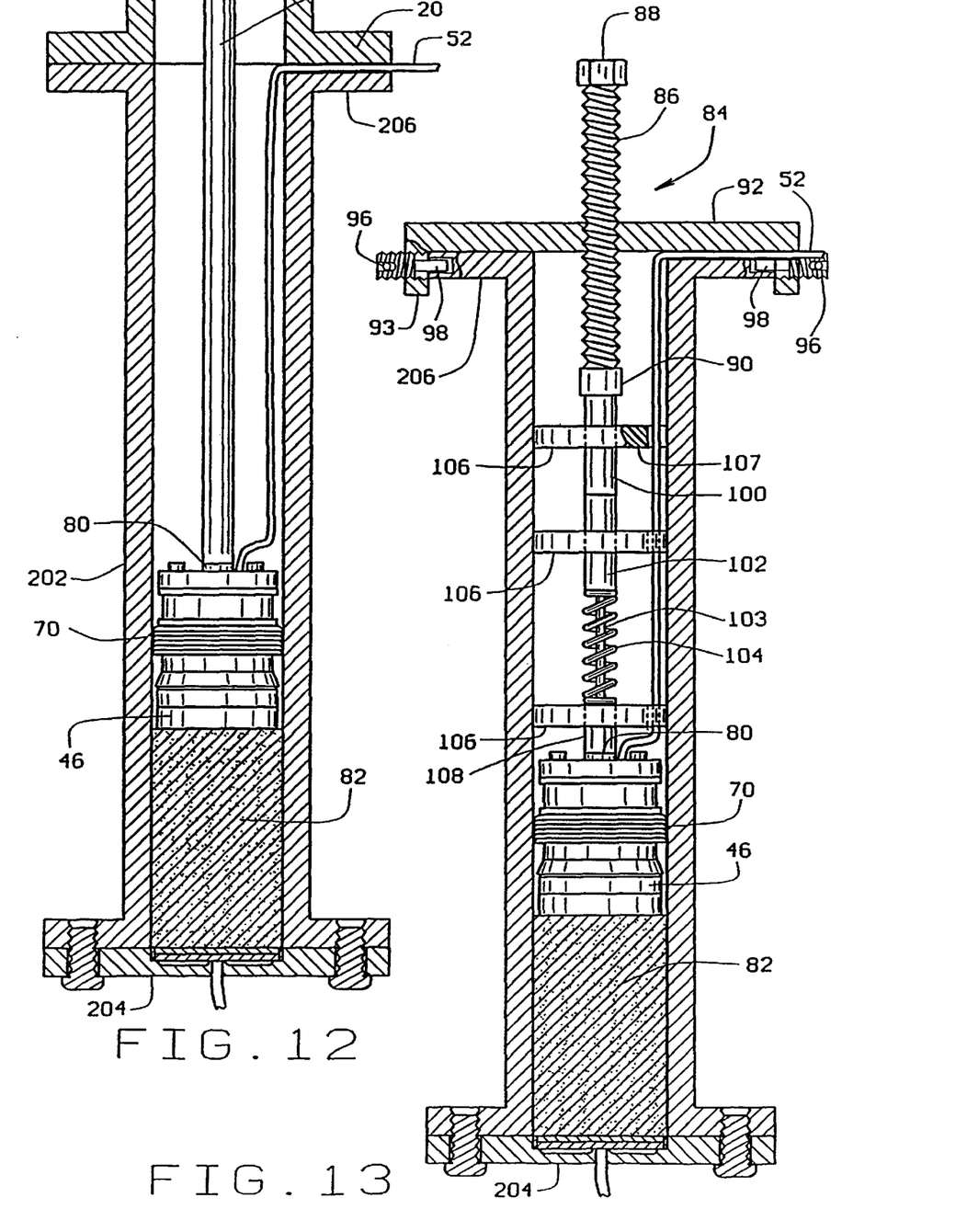
FIG. 12 is a longitudinal section view of the assembly of FIG. 11 showing the piston fully compressed.
FIG. 13 is a longitudinal section view of the assembly of FIG. 12 in which the piston is held in place and pressure is continued to be provided on the chromatographic medium in accordance with another aspect of the invention.

Referring now to FIG. 12, which shows column 202 in engagement with a pressing apparatus with rod 223 compressing piston 46 downward into column 202, it is seen that an end of rod 223 engages pusher head 83 at preferably at least a central portion 80 of pusher head 83. During compression (and during use, if the column 202 is used without removal from the pressing apparatus), feeding tube 52 is preferably held in place in a groove or other passageway to prevent its being crushed between plates 206 and 20.

According to another aspect of the invention, chromatographic column 202 may be removed from the pressing apparatus in a compressed, ready-to-use state, and used separately from the pressing apparatus. If the central portion 80 of pusher head 83 is not threaded or otherwise fixedly attached to rod 223, when rod 223 is withdrawn from column 202, piston 46 will remain in position at column 202 because of the compressive frictional force of the V-rings against the inside of column 202. Chromatographic column 202 itself may be removed in the illustrated embodiment by reversing the motions used to attach it (see FIGS. 2–5 and the description of these Figures above). Once detached, an elastic pressure assembly is inserted into column 202 (perhaps with one or more spacers, depending upon the length of the spring assembly and the extent to which piston 46 is pushed into column 202) and a torque mechanism 84 is fitted at the open end of column 202 to maintain pressure on the spring, and in turn, on piston 46. It is important to maintain pressure on piston 46 with a source of elastic pressure such as a spring, since it has been determined that undesired voids may otherwise form in the compressed chromatographic medium 82 as it settles or is disturbed by the passage of fluid. With elastic spring pressure applied, the creation of voids in the compressed or packed column is avoided.

A preferred elastic pressure assembly that utilizes a spring to exert elastic pressure is shown in FIG. 13, although it should be understood that, as alternatives, any other type of assembly that allows feeding tube 52 to pass through the column and that provides elastic or spring pressure on piston 46 may be used. The illustrated assembly comprises a rigid rod 108 that is dimensioned to allow compressive engagement of central portion 80 of pusher head 83 (other parts of which are not shown in FIG. 13) when the spring assembly is inserted in column 202, a spring 104, one end of which is attached to rod 108, that can be compressed to provide spring pressure, and another rod 102 attached to an opposite end of spring 104. Also provided are rings 106 that provide sliding engagement of the spring assembly into column 102. Rings 106, which may comprise PTFE, each have slots 107 for the passage of feeder tube 52. A thin rod 103 can be provided inside spring 104 to provide greater integrity to the assembly, or more specifically, to guide the compression of spring 104. Thin rod 103 can be integral to or threaded into one of rods 102 and 108 and can be slidingly engaged in a cylindrical passageway of the other one of rods 102 and 108 to accommodate dimensional changes caused by the compression of spring 104. Depending upon the amount of space to be filled in column 202, one or more spacers 100 may also be required. Spacers 100 may be provided in also a variety of lengths, one or more of which may be selected for insertion into column 202 as required. Spacers 100 are also provided with rings 106 that slidingly engage spacers 100 into column 202 and permit passage of feeder tube 52 out of the column. Spacers 100 may, but need not, be fixedly attachable to one another and/or to the rods that are attached to spring 104 such as by threaded rods and tapped holes. It will be recognized that other configurations of spring spacers are possible.

After the elastic pressure assembly is inserted into the chromatographic column 202, a torque mechanism 84 is fitted on the end plate 206 of column 202. Torque mechanism 84 may comprise any assembly that clamps onto or otherwise is affixed to end 206 of column 202 and that provides adjustable pressure on the spring column, either directly or through pressure on or more spacers 100 inserted into column 202. In the embodiment shown in FIG. 13, torque mechanism 84 comprises a plate 92 that covers plate 206 on one end of column 202, and that has wings 93 that fit over opposite edges of plate 206. To provide a firm grip on end plate 206 to allow pressure to be applied to spacer 100 by end 90 of a threaded bolt 86 passing through a central tapped hole of plate 92, spring loaded pins 96 through wings 93 are provided that can be pressingly and removably engaged in corresponding holes 98 in the side of plate 206. Once the pins 96 are holding plate 92 in place, the end 88 of bolt 86 is torqued to provide the desired pressure on the spring assembly inside the column 202.

It will be recognized that the invention provides a number of significant advantages over previous chromatographic columns and methods of using and filling such columns. First, because piston 46 need not be fixedly attached to compression rod 223, and because the piston can be held in column 202 after the rod is retracted, and further because pressure continues to be supplied to the piston 46 by a spring assembly and a torque mechanism, the chromatographic column can be used without being attached or otherwise coupled to the pressing apparatus. Also advantageously, the column can be kept essentially free from internal voids in the compressed chromatographic medium 82 because of the elastic pressure applied in the inventive apparatus. Before compression, the slurry medium can be agitated for thorough mixing after it is placed in the column (as in FIG. 2) and the piston inserted into the column, by rocking of column 202 in the direction of arrow A as shown in FIGS. 2 and 4, and in the opposite direction. Furthermore, if the pressing apparatus is provided with a rotating joint 42 as in FIGS. 6 and 7, not only can this mixing be done while the column is firmly attached to the pressing apparatus, but the column can be operated with pressure applied from the pressing apparatus in either an upward or downward direction (or in any other direction in which the column can be held in place). In addition, the column can be emptied more conveniently than was previously possible by pushing the compressed medium out of the column while it is mounted on the pressing apparatus and turned in a direction in which the slurry drops directly into a collection bucket.

Many modifications and variations of the above embodiments are possible within the spirit and scope of the invention, as will be appreciated by those skilled in the art upon reading this description. Thus, the scope of the invention is not intended to be limited to the details of the embodiments recited above, but rather is intended to include all of that which is properly encompassed by the claims below, including the full range of equivalents allowed under applicable law.

What is claimed is:

1. A chromatographic device comprising:
   a chromatographic column having a hollow tube with first and second opposite open ends, a mounting member secured to the column generally adjacent the first end, and an end cap covering the second end;
   a piston slidable within the tube; and
   a pressing apparatus having a column receiving portion engageable with the mounting member of the chromatographic column, and a pressing mechanism adjacent the column receiving portion;
   the column receiving portion of the pressing apparatus and the mounting member of the chromatographic column being shaped and configured for pivotal movement of the chromatographic column relative to the pressing apparatus between an open position in which the first end of the tube is spaced from the pressing apparatus and a closed position in which the first end of the tube is adjacent the pressing apparatus, the column being moveable relative to the pressing apparatus to an aligned position in which the first end of the tube is aligned with the pressing mechanism, the pressing mechanism being configured for pressing the piston into the tube and toward the second end of the tube.

2. The device of claim 1 wherein the aligned position of the column is different from the closed position.

3. The device of claim 2 wherein the column receiving portion of the pressing apparatus and the mounting member of chromatographic column are shaped and configured for sliding movement of the mounting member on the column receiving portion between the closed position and the aligned position.

4. The device of claim 1 wherein the pressing mechanism comprises a telescoping rod moveable between a retracted position and an extended position, wherein the piston is pressed towards the second end of the tube when the column is in the closed position and the telescoping rod is extended.

5. The device of claim 4 wherein the piston is separate from the telescoping rod and configured to be insertable into the chromatographic column and into sliding, sealing engagement therewith, so that the telescoping rod engages the piston within the chromatographic column when the pressing apparatus is operated to extend the telescoping rod, and is disengaged from the piston when the pressing apparatus is operated to retract the telescoping rod.

6. The device of claim 4 and further comprising a elastic pressure assembly and a torque mechanism,
   the elastic pressure assembly being configured to be insertable into the first end of the chromatographic column after the pressing apparatus is operated to push the piston into the column, the telescoping rod is retracted, and the chromatographic column disengaged from the column receiving portion; and
   the torque mechanism being configured to be secured to the chromatographic column after the disengagement from the column receiving portion and to apply an adjustable pressure to the elastic pressure assembly and to thereby apply an adjustable elastic pressure to the piston.

7. The device of claim 6 wherein the piston comprises at least one bolt operably coupled to a plurality of rings mounted circumferentially about the piston, and the piston is configured for adjustable sliding, sealing engagement inside the chromatographic column, the tightness of the engagement being set by torque applied to the at least one bolt to compress the plurality of rings.

8. The device of claim 4 wherein the column receiving portion is coupled to the pressing apparatus via a rotating joint capable of rotation into a plurality of positions while in engagement with the mounting member of the chromatographic column.

9. The device of claim 1 wherein the end cap includes a liquid passageway, at least one porous frit in fluid communication with the liquid passageway, and a seat in which the at least one porous frit is mounted, the seat including a surface at which the liquid passageway has an opening, the surface also having radial grooves radiating from the opening of the liquid passageway.

10. The device of claim 1 wherein the piston includes a liquid passageway, at least one porous frit in fluid communication with the liquid passageway, and a seat in which the at least one porous frit is mounted, the seat including a surface at which the liquid passageway has an opening, the surface also having radial grooves radiating from the opening of the liquid passageway.

11. The device of claim 1 wherein the piston includes a liquid passageway, at least one porous frit in fluid communication with the liquid passageway, a circumferential O-ring surrounding the at least one porous frit, and a seat in which the at least one porous frit and circumferential o-ring are mounted, the liquid passageway having an opening at a surface of the seat.

12. A chromatographic device comprising:

a piston;

a chromatographic column comprising a hollow tube with first and second opposite open ends, a mounting member secured to the column generally adjacent the first end, and an end cap covering the second end; and a pressing apparatus having a column receiving portion engageable with the mounting member of the chromatographic column, and a telescoping rod moveable between a retracted position and an extended position;

wherein the piston is pressed towards the second end of the tube when the column is in the closed position and the telescoping rod is extended and the piston is separate from the telescoping rod and insertable into the chromatographic column and into sliding, sealing engagement therewith, so that the telescoping rod engages the piston within the chromatographic column when the pressing apparatus is operated to extend the telescoping rod, and is disengaged when the pressing apparatus is operated to retract the telescoping rod.

13. The device of claim 12 and further comprising an elastic pressure assembly and a torque mechanism, the elastic pressure assembly being configured to be insertable into the first end of the chromatographic column after the pressing apparatus is operated to push the piston into the column, the telescoping rod is retracted, and the chromatographic column disengaged from the column receiving portion; and the torque mechanism being configured to be secured to the chromatographic column after the disengagement from the column receiving portion and to apply an adjustable pressure to the elastic pressure assembly and to thereby apply an adjustable elastic pressure to the piston.

14. The device of claim 13 wherein the piston comprises at least one bolt operably coupled to a plurality of rings mounted circumferentially about the piston, and is configured for adjustable sliding, sealing engagement inside the chromatographic column, the tightness of the engagement being set by torque applied to the at least one bolt to compress the plurality of rings.

15. The device of claim 12 wherein the column receiving portion is coupled to the pressing apparatus via a rotating joint capable of rotation into a plurality of positions while in engagement with the mounting member of the chromatographic column.

16. The device of claim 12 wherein the end cap includes a liquid passageway, at least one porous frit in fluid communication with the liquid passageway, and a seat in which the at least one porous frit is mounted, the seat including a surface at which the liquid passageway has an opening, the surface having radial grooves radiating from the opening of the liquid passageway.

17. The device of claim 12 wherein the piston includes a liquid passageway, at least one porous frit in fluid communication with the liquid passageway, and a seat in which the at least one porous frit is mounted, the seat including a surface at which the liquid passageway has an opening, the surface also having radial grooves radiating from the opening of the liquid passageway.

18. The device of claim 12 wherein the piston includes a liquid passageway, at least one porous frit in fluid communication with the liquid passageway, a circumferential O-ring surrounding the at least one porous frit, and a seat in which the at least one porous frit and circumferential o-ring are mounted, the liquid passageway having an opening at a surface of the seat.

19. A chromatographic device comprising:

a chromatographic column having a hollow tube with first and second opposite open ends, a mounting member secured to the column generally adjacent the first end, and an end cap covering the second end;

a piston slidable within the tube; and a pressing apparatus having a stationary portion, a column receiving portion engageable with the mounting member of the column to securely hold the column, and a pressing mechanism adjacent the column receiving portion and configured for moving the piston inside the column when the column is securely held by the column receiving portion, the column receiving portion and pressing mechanism being operatively connected to the stationary portion for pivotable movement of the column receiving portion between different first and second positions, the pressing apparatus being configured to push the piston within the tube towards the second end of the hollow tube when the column receiving portion and pressing mechanism are in the first position and in the second position.

20. The device of claim 19 wherein the piston is pushed in opposite directions when the column receiving portion is in the first and second positions, wherein the orientation of the tube secured to the column receiving portion in the first and second positions is such that, in both the first and second positions, the piston inside the tube is pushed towards the second end of the tube.

21. The device of claim 19 wherein the column receiving portion of the chromatographic column is shaped and configured for pivotal movement of the chromatographic column relative to the pressing apparatus between an open position in which the first end of the tube is spaced from the pressing apparatus and a closed position in which the first end of the tube is adjacent the pressing apparatus, the column being moveable relative to the pressing apparatus to an aligned position in which the first end of the tube is aligned with the pressing mechanism.

22. The device of claim 21 wherein the aligned position of the column is different from that of the closed portion.

23. The device of claim 22 wherein the column receiving portion of the pressing apparatus and the mounting member of the chromatographic column are shaped and configured for sliding movement of the mounting member on the column receiving portion between the closed position and the aligned position.

* * * * *